(12) United States Patent
Redmond et al.

(10) Patent No.: US 7,892,530 B2
(45) Date of Patent: Feb. 22, 2011

(54) TREATMENT OF TUMOR METASTASES AND CANCER

(75) Inventors: H. Paul Redmond, Cork (IE); Rolf W. Pfirrmann, Weggis (CH)

(73) Assignee: ED. Geistlich Soehne AG Fuer Chemische Industrie, Wolhusen (CH)

( * ) Notice: Subject to any disclaimer, the term of this patent is extended or adjusted under 35 U.S.C. 154(b) by 350 days.

(21) Appl. No.: 11/526,245

(22) Filed: Sep. 25, 2006

(65) Prior Publication Data

US 2007/0065400 A1 Mar. 22, 2007

Related U.S. Application Data

(60) Continuation-in-part of application No. 09/983,279, filed on Oct. 23, 2001, now abandoned, and a continuation-in-part of application No. 10/424,102, filed on Apr. 28, 2003, which is a continuation of application No. 10/281,138, filed on Oct. 28, 2002, now Pat. No. 6,815,441, which is a division of application No. 09/583,902, filed on Jun. 1, 2000, now Pat. No. 6,479,481.

(60) Provisional application No. 60/243,409, filed on Oct. 27, 2000, provisional application No. 60/137,421, filed on Jun. 4, 1999, provisional application No. 60/151,050, filed on Aug. 27, 1999, provisional application No. 60/167,681, filed on Nov. 29, 1999, provisional application No. 60/174,607, filed on Jan. 5, 2000, provisional application No. 60/182,200, filed on Feb. 14, 2000.

(51) Int. Cl.
*A61K 38/19* (2006.01)
*A61K 31/54* (2006.01)

(52) U.S. Cl. .................................. 424/85.2; 514/222.5

(58) Field of Classification Search ........................ None
See application file for complete search history.

(56) References Cited

U.S. PATENT DOCUMENTS

| | | |
|---|---|---|
| 504,243 A | 8/1893 | Philippot |
| 1,039,140 A | 9/1912 | Kampfe |
| 1,188,697 A | 6/1916 | Steinberg |
| 1,461,366 A | 7/1923 | Mulford et al. |
| 1,676,146 A | 7/1928 | Krafft |
| 2,021,465 A | 11/1935 | Ritscher |
| 2,609,960 A | 9/1952 | Irwin |
| 2,643,024 A | 6/1953 | Cronheim |
| 2,760,672 A | 8/1956 | Cronheim |
| 3,598,105 A | 8/1971 | Cristaldi |
| 3,809,064 A | 5/1974 | Ziegler |
| 3,961,443 A | 6/1976 | Insalaco |
| 4,000,830 A | 1/1977 | French |
| 4,350,156 A | 9/1982 | Malchesky et al. |
| 4,467,784 A | 8/1984 | Lee et al. |
| 4,482,077 A | 11/1984 | Henderson |
| 4,626,536 A | 12/1986 | Pfirrmann |
| 4,654,345 A | 3/1987 | Cavanak |
| 4,828,140 A | 5/1989 | Henderson |
| 4,960,415 A | 10/1990 | Reinmuller |
| 5,077,281 A | 12/1991 | Reinmüller |
| 5,167,960 A | 12/1992 | Ito et al. |
| 5,176,651 A | 1/1993 | Allgood et al. |
| 5,191,900 A | 3/1993 | Mishra |
| 5,208,018 A * | 5/1993 | Gough ...................... 424/85.2 |
| 5,210,083 A | 5/1993 | Pfirrmann |
| 5,262,403 A | 11/1993 | Nicolson et al. |
| 5,362,754 A | 11/1994 | Raad et al. |
| 5,416,091 A | 5/1995 | King |
| 5,441,481 A | 8/1995 | Mishra et al. |
| 5,554,148 A | 9/1996 | Aebischer et al. |
| 5,593,665 A | 1/1997 | Pfirrmann et al. |
| 5,696,153 A | 12/1997 | Ainsworth et al. |
| 5,725,553 A | 3/1998 | Moenning |
| 5,730,045 A | 3/1998 | Delaquis et al. |
| 5,749,859 A | 5/1998 | Powell |
| 5,763,421 A | 6/1998 | Caretto et al. |
| 5,819,748 A | 10/1998 | Pfirrmann |
| 5,881,905 A | 3/1999 | Brady |
| 5,889,183 A | 3/1999 | Herdeis et al. |
| 5,957,038 A | 9/1999 | Shimazaki |
| 5,960,415 A | 9/1999 | Williams |
| 6,011,030 A | 1/2000 | Pfirrmann |
| 6,029,843 A | 2/2000 | Kroscher et al. |
| 6,030,358 A | 2/2000 | Odland |
| 6,035,766 A | 3/2000 | Schirmer |

(Continued)

FOREIGN PATENT DOCUMENTS

CA 2302720 A1 9/2000

(Continued)

OTHER PUBLICATIONS

Negrier et al (Eur J Cancer Clin Oncol, 1989, vol. 25, suppl 3, pp. S21-S28).*

(Continued)

*Primary Examiner*—Karen A Canella
(74) *Attorney, Agent, or Firm*—Rothwell, Figg, Ernst & Manbeck, P.C.

(57) ABSTRACT

Tumor metastases in cancer patients are inhibited by administration of a combination therapy including effective amounts of Interleukin-2 and a methylol transfer agent such as taurolidine, taurultam or mixtures thereof.

16 Claims, No Drawings

U.S. PATENT DOCUMENTS

| | | | |
|---|---|---|---|
| 6,080,397 A | 6/2000 | Pfirrmann |
| 6,093,180 A | 7/2000 | Elsberry |
| 6,105,811 A | 8/2000 | Alfred |
| 6,117,868 A | 9/2000 | Pfirrmann |
| 6,166,007 A | 12/2000 | Sodemann |
| 6,258,797 B1 | 7/2001 | Lehner |
| 6,303,596 B1 | 10/2001 | Morrissey et al. |
| 6,429,224 B1 | 8/2002 | Calabresi et al. |
| 6,479,481 B1 | 11/2002 | Stendel et al. |
| 6,521,616 B2 | 2/2003 | Calabresi et al. |
| 6,546,849 B1 | 4/2003 | Shimazaki |
| 6,617,333 B2 | 9/2003 | Rabindran et al. |
| 6,688,487 B2 | 2/2004 | Oakes et al. |
| 6,815,441 B2 | 11/2004 | Stendel et al. |
| 6,821,968 B2 | 11/2004 | Pfirrmann |
| 6,995,164 B2 | 2/2006 | Calabresi et al. |
| 2001/0031870 A1 | 10/2001 | Soll et al. |
| 2002/0052366 A1 | 5/2002 | Calabresi et al. |
| 2002/0091123 A1 | 7/2002 | Redmond et al. |
| 2002/0098164 A1 | 7/2002 | Redmond et al. |
| 2002/0111328 A1 | 8/2002 | Redmond et al. |
| 2002/0111345 A1 | 8/2002 | Calabresi et al. |
| 2002/0131935 A1 | 9/2002 | Fisher et al. |
| 2003/0027818 A1 | 2/2003 | Redmond et al. |
| 2003/0092707 A1 | 5/2003 | Redmond et al. |
| 2003/0195198 A1 | 10/2003 | Stendel et al. |
| 2004/0087579 A1 | 5/2004 | Redmond et al. |

FOREIGN PATENT DOCUMENTS

| | | | |
|---|---|---|---|
| CA | 2393159 A1 | 6/2001 |
| CA | 2393252 A1 | 6/2001 |
| CH | 587040 A5 | 4/1977 |
| DE | 3536560 A1 | 4/1986 |
| DE | 19606897 A1 | 8/1997 |
| EP | 0048558 A2 | 3/1982 |
| EP | 0139535 A2 | 5/1985 |
| EP | 0147021 A1 | 7/1985 |
| EP | 0253662 A1 | 1/1988 |
| EP | 1040841 A1 | 10/2000 |
| EP | 1 066 830 A2 | 1/2001 |
| EP | 1247524 A1 | 10/2002 |
| EP | 1201247 A2 | 5/2005 |
| GB | 2165752 A | 4/1986 |
| JP | 60-105618 A | 6/1985 |
| JP | 61-000017 A | 1/1986 |
| JP | 63-72626 A | 4/1988 |
| JP | 5-500973 A | 2/1993 |
| JP | 5-505615 A | 8/1993 |
| JP | 2000-300661 A | 10/2000 |
| JP | 2000-516196 A | 12/2000 |
| JP | 2001-10976 A | 1/2001 |
| JP | 2002-326936 A | 11/2002 |
| WO | WO 88/05301 A1 | 7/1988 |
| WO | WO 91/13628 A1 | 9/1991 |
| WO | WO 92/00743 | 1/1992 |
| WO | WO 92/00743 A1 | 1/1992 |
| WO | WO 95/18638 A1 | 7/1995 |
| WO | WO 95/30423 A2 | 11/1995 |
| WO | WO 97/25052 A2 | 7/1997 |
| WO | WO 98/28027 A1 | 7/1998 |
| WO | WO 98/39354 A1 | 9/1998 |
| WO | WO 98/52572 A1 | 11/1998 |
| WO | WO 99/06114 A2 | 2/1999 |
| WO | WO 00/01391 A1 | 1/2000 |
| WO | WO 01/39762 A2 | 6/2001 |
| WO | WO 01/39763 A2 | 6/2001 |
| WO | WO 02/07810 A2 | 1/2002 |

OTHER PUBLICATIONS

Abstract of Jacobs et al., *Cancer Res.*, 1986, vol. 46, 4 pt 2, pp. 2101-2104.

Abstract of Kimura et al., *Cancer*, 1997, vol. 80, pp. 42-49.

Abstract of Negrier et al., *Eur. J. Cancer Clin. Oncol.*, 1989, vol. 25, suppl. 3, pp. S21-S28.

Abstract of Okuno et al., *Hepato-Gastroenterology*, Mar.-Apr. 1999, vol. 46, pp. 1116-1121.

Abstract of Salmaggi et al., *Italian Journal of Neurological Sciences*, 1996, vol. 17, pp. 267-276.

Anderson et al., *Journal of Clinical Investigation*, 1996, vol. 97, pp. 1952-1959.

Bedrosian I. et al., Taurolidine, an analogue of the amino acid taurine, suppresses interleukin 1 and tumor necrosis factor synthesis in human peripheral blood mononuclear cells. *Cytokine*, 1991; 3(6):568-575.

Blum et al., *European Journal of Medicine*, Jan. 2001, vol. 36, pp. 63-74.

Clarke, K. et al., KRN8602 (MX2-hydrochloride): an active new agent for the treatment of recurrent high-grade glioma, *J Clin Oncol* Aug. 1999; 17(8) 2579-2584.

Dimmock et al., "Mannich bases of phenolic azobenzenes possessing cytotoxic activity," *Eur. J. Med. Chem.*; 1997, vol. 32, pp. 583-594.

Edwards et al., *Journal of Clinical Investigation*, 1992, vol. 90, pp. 637-641.

Jacobi, C.A. et al., Inhibition of Peritoneal Tumor Cell Growth and Implantation in Laparoscopic Surgery in a Rat Model, *Am J of Surgery*, 174, Sep. 1997, 359-363.

Jacobi, C.A. et al., Intraperitoneal installation of taurolidine and heparin for the prevention of intraperitoneal tumor growth and trocar metastases in laparoscopic surgery in a rat model, *Langenbecks Arch Chir* (1997) 382 [Suppl 1]: S31-S36.

Mccourt, M. et al., Taurolidine inhibits tumor cell growth *in vitro* and *in vivo*, *Annals of Surgical Oncology*, 2000; 7(9):685-691.

Monson, J.R.T., et al., "Abrogation of tumor necrosis factor (TNF) toxicity in the murine model by taurolidine: support for synergism of TNF with endotoxin," *Br. J. Surg.*, 1990; 77(6):A708.

Monson, J.R.T., "Malignant melanoma: a plague of our times," *Br. J. Surg.*, 1989; 76:997-998.

Monson, J.R.T. et al., Preliminary evidence that taurolidine is anti-neoplastic as well as anti-endotoxin and anti-microbial, *Br. J. Surg.*, 77(6), Jun. 1990, A711.

Monson, J.R.T. et al., Taurolidine as an anti-neoplastic agent: a previously undiscovered role?, *Br. J. Surg.*, 77(12), Dec. 1990, 1432.

Monson, J.R.T. et al., "Taurolidine inhibits tumour necrosis factor (TNF) toxicity—new evidence of TNF and endotoxin synergy," *European Journal of Surgical Oncology*, 1993; 19:226-231.

Nudelman et al., *European Journal of Medicine*, Jan. 2001, vol. 36, pp. 63-74.

Merck Manual, 17th Edition, Japanese Version, Nikkei BP, p. 1921, 1999.

Med. J. Kinki Univ., Kinki University medical conference, vol. 25, 1, p. 17A, 2000.

Endoh, "Effects of recombinant Interleukin-2 (rIL-2) for recurrent and metastatic renal cell carcinoma." Biotherapy 5(6):1100-1106, 1991.

Lung Cancer, the 38th Japan Lung cancer conference, The Japan Lung Cancer Society, vol. 37(5):765, 1997.

Thatcher, et al. "Recombinant interleukin-2 (rIL-2) given intrasplenically and intravenously for advanced malignant melanoma. A phase I and II study." Br. J. Cancer, 60(5):770-774, 1989.

Glesby et al., "Pilot Study of Low Dose Daily Interleukin-2 Plus Pegylated-Interferon-alfa-2b and Ribavirin in Patients with HCV/HIV Co-Infection: ACTG A5088," 11th Conf Retrovir Opportunistic Infect, Abstract No. 818, 2004, San Francisco, CA, Feb. 8-11, 2004.

Institute of Pharmacology University of Zurich, Research Report, "Taurolin Suppresses Activity of Tumor Necrosis Factor-$\alpha$ in vivo", pp. 1-9, 1993.

O'Brien et al., "Co-immunotherapy with Interleukin-2 and Taurolidine for Progressive Metastatic Melanoma," Irish Journal of Medical Science, vol. 175, No. 1, pp. 2-5 (2006).

Smith et al., "New Strategies to Combat HIV: Augmenting Antiviral Immunity," AIDS Read. 2003 (8) 365-9, 382.

Smith, Interleukin 2 Toxicity & Standard Procedures for Recording & Reporting Drug Toxicities, 2000.

Canadian Office Action from CA appln. No. 2,379,734 dated Sep. 29, 2008, 3 pages.

European Search Report from EP appln. No. 01 30 9983 dated Apr. 9, 2003, 4 pages.

Japanese Office Action for JP appln 2002-280476 entitled "Preliminary Notice of Reasons for Rejection", Dec. 4, 2008, and English language translation, pp. 1-7.

Ananthan, in *Cancer Chemotherapeutic Agents*, Foye (Ed.), American Chem. Soc., Washington, D.C. (1995) pp. 49-58.

Braumann et al., "High Doses of Taurolidine Inhibit Advanced Intraperitoneal Tumor Growth in Rats" *J. Surg. Res.* 129: 129-135, 2005.

Braumann et al., "Prevention of disease progression in a patient with a gastric cancer-re-recurrence. Outcome after intravenous treatment with the novel antineoplastic agent taurolidine. Report of a case" *World J. Surg. Oncol.* 4(34): 6 pages, 2006.

Calabresi et al., "Taurolidine: Cytotoxic and Mechanistic Evaluation of a Novel Antineoplastic Agent" *Can. Res.* 61: 6816-6821, 2001.

Campbell et al., "The Role of Tumor Rejection Antigens in Host Antitumor Defense Mechanisms" *Cancer*, 75(11): 2649-2655, 1995.

Carter et al., *Chemotherapy of Cancer*, Second Ed., John Wiley & Sons, New York, 71-78, 1981.

Da Costa et al., "The effect of laparotomy and laparoscopy on the establishment of spontaneous tumor metastases" *Surgery*, 124(3): 516-525, 1998.

Da Costa et al., "Laparotomy and laparoscopy differentially accelerate experimental flank tumour growth" *Br. J. Surg.* 85: 1439-1442, 1998.

Da Costa et al., "Taurolidine Improves Survival by Abrogating the Accelerated Development and Proliferation of Solid Tumors and Development of Organ Metastases from Circulating Tumor Cells Released Following Surgery" *J. Surg. Res.* 101:111-119, 2001.

Darnowski et al., "Mechanistic and antineoplastic evaluation of taurolidine in the DU145 model of human prostate cancer" *Can. Chemother. Pharmacol*, 54: 249-258, 2004.

Erb et al., "Structural Investigation of a New Organic Antiseptic: Taurolidine", *Talanta*, 29: 953-958, 1982.

Erb et al., "Structural investigation of a new organic antiseptic: Taurolidine Analytical study and application to identification and quantitation in biological fluids" *Eur. J. Drug Metab. Pharm.* 8(2): 163-173, 1983.

Fanning et al., "Inhibition of neutrophils apoptosis after elective surgery" *Surgery*, pp. 527-534, 1999.

Fiedler, in *Lexikon der Hilfsstoffe für Pharmazie, Kosmetik und angrenzende Gebiete*, Editio Cantor Aulendorf, 695, 1985.

Finnegan et al., "Taurine Attenuates Recombinant Interleukin-2-Activated, Lymphocyte-Mediated Endothelial Cell Injury" *Cancer*, 82(1): 186-199, 1998.

Gallagher et al., "Hepatic Resection of Solitary Metastasis from Transitional Cell Carcinoma of the Bladder" *J. Urology*, 159: 986, 1998.

Gugenheim et al., "Laparoscopic Resection of Solid Liver Tumours" *Br. J. Surg.*, 83: 334-335, 1996.

Gavrovskaya et al., "Antihypoxic Properties of Taurinamide Derivatives: The Experimental Study" *Taurine*, 6: 523-528, 2006.

Hansen et al., "Altretamine" *The Annals of Pharmacotherapy*, 25:146-152, 1991.

Hood et al., "Studies of the thiadiazine, Taurolidine- I. Identification of the Molecular Species Present in Aqueous Solutions by $^1$H- and $^{13}$C-NMR Spectroscopy" *Talanta*, 41(1): 107-113, 1994.

Huscher et al., "Laparoscopic Colorectal Resection" *Surg. Endosc.* 10: 875-879, 1996.

Jacobi et al., "Influence of different gases and intraperitonial instillation of antiadherent or cytotoxic agents on peritoneal tumor cell growth and implantation with laparoscopic surgery in a rat model" *Surg. Endosc.*, 13: 1021-1025, 1999.

Jacobi et al., "New Therapeutic Strategies to Avoid Intra- and Extraperitoneal Metastases during Laparoscopy: Results of a Tumor Model in a Rat" *Dig. Surg.*, 16: 393-399, 1999.

Jacobi et al., "Taurolidine- a new drug with anti-tumor and anti-angiogenic effects" *Anti-Cancer Drugs*, 16(9): 917-921, 2005.

Janik et al., "Prevention of Postoperative Peritoneal Adhesions, Efficacy of Povidone" *Arch Surg.*, 117: 1321-1324, 1982.

*The Japanese Journal of Gastroenterological Surgery*, 23(2): 3 pages, 1990.

*The Japanese Journal of Gastroenterological Surgery*, 30(6): 3 pages, 1997.

Johnston et al., "Taurolin for the Prevention of Parenternal Nutrition Related Infection: Antimicrobial Activity and Long-Term Use" *Clin. Nutr.* 12(6): 365-368, 1993.

Kilian et al., "Effects of taurolidine and octreotide on tumor growth and lipid peroxidation after staging-laparoscopy in ductal pancreatic cancer" *Prostaglandins, Leukotrienes and Essential Fatty Acids*, 69: 261-267, 2003.

Kilian et al., "Impact of taurolidin and octreotide on liver metastasis and lipid peroxidation after laparoscopy in chemical induced ductal pancreatic cancer" *Investigational New Drugs*, 23: 157-164, 2005.

Kirsch et al., "The Effect of Polyvinylpyrrolidine on the Stability of Taurolidine" *Pharm. Devel. and Tech.*, 2(4): 345-356. 1997.

Koike et al., "Effect of 48-hour Continuous Intravenous Injection of 5-Flouorouracil (5-FU) for Hematogenous Metastasis of Large Intestine Carcinoma" *Jap. J. Gastro. Surg.* 24(2): 1-3, 1991 (partial English translation).

Koldehoff et al., "Taurolidine is effective in the treatment of central venous catheter-related bloodstream infections in cancer patients" *Intl. J. Antimicrobial Agents*, 24: 491-495, 2004.

Kopple et al., "Effect of Intravenous Taurine Supplementation on Plasma, Blood Cell, and Urine Taurine Concentrations in Adults Undergoing Long-term Parenteral Nutrition" *Am. J. Clin. Nutr.*, 52(5): 846-853, 1990.

Lucarotti et al., "Antiseptic Toxicity to breast carcinoma in tissue culture an adjuvant to conservation therapy" *Ann. Roy. Coll. of Surg. of Eng.*, 72: 388-392, 1990.

McNamara et al., "Significance of angiogenesis in cancer therapy" *Br. J. Surg.* 85: 1044-1055, 1998.

Medical Encyclopedia: Electrolytes http://www.nlm.nih.gov/medlineplus/ency/article/002350.htm, 1, 2001. Accessed May 31, 2007.

Medical Encyclopedia: Protein in diet http://www.nlm.nih.gov/medlineplus/print/ency/article/002467.htm, 1-2, 2001. Accessed May 31, 2007.

Mughal et al., "Infected Feeding Lines" *Care Critically III* 6(6): 228-231, 1990.

Nestler et al., "Impact of taurolidine on the growth of CC531 colon carcinoma cells in vitro and in a laparoscopic animal model in rats" *Surg. Endosc.*, 19: 280-284, 2005.

Nici et al., "The Effects of Taurolidine, a Novel Antineoplastic Agent, on Human Malignant Mesothelioma" *Clin. Can. Res.* 10: 7655-7661, 2004.

Opitz et al., "The influence of adhesion prophylactic substances and taurolidine/heparin on local recurrence and intraperitoneal tumor growth after laparoscopic-assisted bowel resection of colon carcinoma in a rat model" Surg. Endosc. 17:1098-1104, 2003.

Parfitt, "Martindale, the complete drug reference, 32$^{nd}$ ed", (formerly Martindale the extra pharmacopoeia, London: Pharmacopoeia), XP-002231711, London: Pharmaceutical press, GB, 534-537, 1999.

Physicians' Desk Reference, "Fluorouracil Product Information", pp. 2034-2036, 1995.

Pidgeon et al., "The role of endotoxin/lipopolysaccharide in surgically induced tumour growth in a murine model of metastatic disease" *Br. J. Canc.* 81(8): 1311-1317, 1999.

Redmond et al., Letter to the Editor, *Annals of Surgery*, 227(2): 309, 1998.

Reinmueller, "Die Beeinflussung der physiologischen und pathologischen Gerinnung durch Taurolidin und Implikationen für die Anwendung" *Zentralbl Chir Suppl*, 4: 13-18, 1999.

Reymond et al., "Feasibility of therapeutic pneumoperitoneum in a large animal model using a microvaporisator" *Surg. Endosc.*, 14: 51-55, 2000.

Ribizzi et al., "Taurolidine: preclinical evaluation of a novel, highly selective, agent for bone marrow purging" *Bone Marrow Transplantation*, 29: 313-319, 2002.

Rodak et al., "Induction of reactive oxygen intermediates-dependent programmed cell death in human malignant ex vivo glioma cells and inhibition of the vascular endothelial growth factor production by taurolidine" *J. Neurosurg.*, 102: 1055-1068, 2005.

Semple et al., "Potent and Selective Thrombin Inhibitors Featuring Hydrophobic, Basic $P_3$-$P_4$-aminoalkyllactam Moieties" *Bioorganic & Medicinal Chemistry Let.* 8: 3525-3530, 1998.

Shrayer et al., "The effect of Taurolidine on adherent and floating subpopulations of melanoma cells" *Anti-Cancer Drugs*, 14(4): 295-303, 2003.

Simon et al., "Diagnosis and treatment of catheter-related infections in paediatric oncology: and update" *Clin. Microbiol. Infect.*, 12(7): 606-620, 2006.

Stapleton et al., "Taurine and human nutrition", *Clin. Nutr.* 16(3):103-8, 1997.

Stapleton et al., "Taurine and Inflammation—A New Approach to an Old Problem?" *J. of Leukocyte Biol.*, 61: 231-232, 1997.

Stendel et al., "The Effect of Taurolidine on Brain Tumor Cells" *Antican. Res.* 22: 809-814, 2002.

Stendel, R. et al., "Enhancement of Fas-ligand-mediated programmed cell death by taurolidine", *Antican. Res.* 23: 2309-2314, 2003.

Stendel et al., "Taurolidine-Fibrin-Sealant-Matrix Using Spray Application for Local Treatment of Brain Tumors" *Antican. Res.* 24: 631-638, 2004.

Stendel et al., "Treatment of Glioblastoma with Intravenous Taurolidine. First Clinical Experience" *Antican. Res.* 24: 1143-1148, 2004.

Suzuki et al., "An Effective Case of Combined Arterial and Portal Infusion Chemotherapy for Sigmoid Colon Cancer with Multiple Liver Metastases" *Jap. Soc. Gastroent. Surg.* 27(5): 1090-1093, 1994.

Treutner et al., "Prevention of Postoperative Adhesions by Single Intraperitoneal Medication" *J. Surg. Res.*, 59(6): 764-771, 1995.

University of Florida Shands Cancer Center: "Electrolyte Imbalance", http://www/ufscc.ufl.edu/Patient/content.aspx?section=ufscc&id-213137 (2006). Accessed May 4, 2006.

Van Gelder, "A Central Mechanism of Action for Taurine: Osmoregulation, Bivalent Cations, and Excitation Threshold" *Neurochem. Res.* 8(5): 687-699, 1983.

Volz, et al., "Modulation of Tumor-Induced Lethality after Pneumoperitoneum in a Mouse Model" *Cancer*, 89(2): 262-266, 2000.

Wakabayashi et al., "Chemotherapy for Brain Tumors", 50(2): 305-312, 2001 (partial English translation).

Wang et al., "Endotoxin/Lipopolysaccharide Activates NF-$_K$B and Enhances Tumor Cell Adhesion and Invasion Through a β1 Integrin-Dependent Mechanism" *J. Immunol.*, vol. 170, pp. 795-804, 2003.

Watson et al., "Taurolidine, an antilipopolysaccharide agent, has immunoregulatory properties that are mediated by the amino acid taurine" *J. Leukocyte Biol.* 58: 299-306, 1995.

Weberschock et al., "Efficacy of Sytemic [sic] Taurolidin Application in the Treatment of Liver Metastases in a Rat Model", Dept. of General and Vascular Surgery, Johann Wolfgang Goethe University, 1 page, 1996-2002 (Abstract).

Wenger et al., "Effects of taurolidine and octreotide on port site and liver metastasis after laparoscopy in an animal model of pancreatic cancer" *Clin. Exp. Metastasis*, 19: 169-173, 2002.

Wicki et al., *Taurolin—A New Concept in Antimicorbial Chemotherapy in Surgical Infection*, Urban &.Schwarzenberg, Munich, 3:244-253, 1985.

Wittich et al., "Irrigation of Port Sites: Prevention of Port Site Metastases?" *J. Laparoendoscopic & Advanced Surg. Tech.* 14(3): 125-129, 2004.

Wördemann et al., "Tumor Necrosis Factor-α Production by Human Hepatoma Cell Lines Is Resistant to Drugs That Are Inhibitory to Macrophages" *J. Interf. and Cytokine Res.* 18: 1069-1075, 1998.

Wu et al., "Neutrophil-induced Transmigration of Tumour Cells Treated with Tumour-conditioned Medium is Facilitated by Granulocyte-macrophage Colony-stimulating Factor" *Eur. J. Surg.*, 166: 361-366, 2000.

Lubec et al., "Decreased Tumor Incidence and Increased Survival by One Year Oral Low Dose Arginine Supplementation in the Mouse" *Life Sci.* 58:2317-2325, 1996.

Anonymous, "Cerebrospinal Fluid" http://uscneurosurgery.com/infonet/glossary/c/cerebrospinal%20/fluid%20csf.htm. 2 pages. Accessed May 31, 2007.

Anonymous, "Cookware FAQ's/Care and Cleaning", http://www.bialetti.com/cook/features/cook carefaq.htm; Apr. 3, 2008.

Anonymous, "Methods of Sterilisation." *British Pharmacopoeia*. vol. 2, Appendix XVIII: A264-A267, 1998.

Araki et al.,*J. Jap. Soc. Gastroenterol. Surg.* 27(5): 1090-1093, 1994.

Blenkharn, "The Antimicrobial Activity of Taurolin®—a Possible New Additive for Parenteral Nutrition Solutions" *Clin. Nutr.* 6(1): 35-38, 1987.

Blum et al., "Hexamethylmelamine—A New Drug with Activity in Solid Tumors" *Eur. J. Cancer*, 9:195-202, 1973.

Braumann et al., "The Influence of Intraoperative Intravenous and Intraperitoneal Application of Taurolidine with Heparin on Subcutaneous and Intraperitoneal Tumor Growth in Laparoscopic Surgery in a Rat Model" Dept. of Surgery, Humboldt-University of Berlin, Campus ChartiéMitte, Schumannstr. 20-21, 10098 Berlin, Germany, Apr. 14$^{th}$ and 15$^{th}$, 2000, 3 pages.

Braumann et al., "Influence of intraperitoneal and systemic application of taurolidine and taurolidine/heparin during laparoscopy on intraperitoneal and subcutaneous tumour growth in rats" *Clin. Exp. Metastasis* 18: 547-552, 2001.

Braumann et al., "Local and systemic chemotherapy with taurolidine and taurolidine/heparin in colon cancer-bearing rats undergoing laparotomy" *Clin. Exp. Metastasis*, 20: 387-394, 2003.

Braumann et al., "The Tumor-Suppressive Reagent Taurolidine Is An Inhibitor Of Protein Biosynthesis" *Int. J. Cancer*, 112: 225-230, 2004.

Braumann et al., "Effects of increasing doses of a bolus injection and an intravenous long-term therapy of taurolidine on subcutaneous (metastatic) tumor growth in rats" *Clin. Exp. Metastasis*, 22: 77-83, 2005.

\* cited by examiner

TREATMENT OF TUMOR METASTASES AND CANCER

CROSS-REFERENCE TO RELATED APPLICATION

The present application is a continuation-in-part of U.S. application Ser. No. 09/983,279, filed Oct. 23, 2001 now abandoned, and claims the benefit of U.S. Provisional Application Ser. No. 60/243,409, filed Oct. 27, 2000. This application also is a continuation-in-part of U.S. application Ser. No. 10/424,102, filed Apr. 28, 2003 which is a continuation of U.S. application Ser. No. 10/281,138, filed Oct. 28, 2002 now U.S. Pat. No. 6,815,441, which is a divisional of U.S. application Ser. No. 09/583,902, filed Jun. 1, 2000, now U.S. Pat. No. 6,479,481 B1, which claims the benefit of U.S. Provisional Application No. 60/137,421 filed Jun. 4, 1999, and which claims the benefit of U.S. Provisional Application No. 60/151,050 filed Aug. 27, 1999, and which claims the benefit of U.S. Provisional Application No. 60/167,681 filed Nov. 29, 1999, and which claims the benefit of U.S. Provisional Application No. 60/174,607, filed Jan. 5, 2000 and which claims the benefit of U.S. Provisional Application No. 60/182,200 filed Feb. 14, 2000.

BACKGROUND OF THE INVENTION

1. Field of the Invention

The present invention relates to the field of treating tumor metastases and cancer.

2. Description of the Background Art

Interleukin-2 (IL-2) is an agent which has been suggested for inhibiting tumor cell growth. However, administration of IL-2 to patients presents severe toxicity problems, since IL-2 elicits an extremely strong systemic inflammatory response syndrome (SIRS) reaction in patients. Toxicity of IL-2 is so severe that approximately 70% of patients cannot tolerate treatment.

Additionally, a common problem in patients undergoing cancer treatment is tumor recurrence or metastasis.

Thus, despite the advances in cancer treatment, there remains a significant need in the art for new and improved cancer treatment therapies.

SUMMARY OF THE INVENTION

In accordance with the present invention, tumor metastasis is inhibited in a cancer patient by administering to said patient a combination therapy comprising effective amounts of IL-2 and a methylol transfer agent.

DETAILED DESCRIPTION OF THE INVENTION

It has surprisingly been found that methylol transfer agents such as taurolidine and taurultam reduce or substantially eliminate the severe toxicity and side effects of IL-2 in a combination therapy for inhibiting tumor metastases and treating cancer in patients, while it has unexpectedly been found that the efficacy of IL-2 is actually enhanced by the methylol transfer agents in the combination therapy of the present invention.

IL-2 when used in accordance with the present invention includes natural or recombinant Interleukin-2, or biologically active derivatives or substantial equivalents thereof.

Methylol transfer agents include methylol-containing compounds such as taurolidine and taurultam. The compounds taurolidine and taurultam are disclosed in U.S. Pat. No. 5,210,083. Other suitable methylol-containing compounds may be found among those identified in PCT Publication No. WO 01/39763. Particularly preferred methylol transfer agents for utilization in accordance with the present invention are taurolidine, taurultam, biologically active derivatives thereof and mixtures thereof.

Particularly preferred embodiments involve treatment of cancers selected from the group consisting of malignant melanoma and renal cancer, and inhibition of tumor metastases thereof. For example, the combination therapy of the present invention has been found to be particularly effective in inhibiting metastatic malignant melanoma and metastatic renal cell carcinoma.

Other cancers to which the combination therapy of the present invention is effective may include other carcinomas, sarcomas or lymphomas. Cancers to which the present invention may be applicable include glioma, neuroblastoma, astrocytoma, carcinomatous meningitis, breast cancer, ovarian cancer, colon cancer, prostate cancer, pancreatic cancer, central nervous system (CNS) cancer, liver cancer, lung cancer, gastric cancer, esophageal cancer, urinary bladder cancer, leukemia, lymphoma, melanoma, renal cell cancer and metastases thereof.

Effective daily dosage amounts of IL-2 may comprise pharmaceutical dosage units within the range of 1,000,000,000 units (U) IL-2 per m2 body surface area. Dosage amounts of IL-2 also may be found within the range of 100,000-1,000,000 U per kilogram body weight. Dosage amounts of IL-2 further may be found within the range of 0.1-100 micrograms IL-2 per kilogram body weight.

Effective dosage amounts of a methylol transfer agent in accordance with the present invention may comprise pharmaceutical dosage units within the range of about 0.1-1,000 mg/kg. Preferred dosages may be in the range of about 10-20 grams taurolidine, taurultam or a mixture thereof, per administration.

Pharmaceutical dosage units of the combined therapy of the present invention may be administered by any suitable route, which include oral, topical or peritoneal administration, e.g., subcutaneously, intraperitoneally, intramuscularly, or intravenously, e.g., by infusion or injection.

In preferred embodiments, 250 ml of taurolidine 2% solution is administered by intravenous infusion about 1-6 times per day, more preferably about 2-4 times per day, during a treatment period, concurrently with administration of about 10,000,000-40,000,000 units m2 IL-2 by intravenous infusion per day during the treatment period.

The present invention also is directed to a combination of IL-2 and a methylol transfer agent, in effective amounts for simultaneous, separate or sequential use for inhibiting tumor metastasis in a cancer patient. The invention also is directed to pharmaceutical combinations including pharmaceutical dosage units comprising effective amounts of Interleukin-2 and a methylol transfer agent for inhibiting tumor metastasis in a cancer patient, as well as to pharmaceutical compositions comprising such combinations.

The invention is further illustrated by the following non-limiting examples.

EXAMPLE 1

A 63 year old patient diagnosed with metastatic malignant melanoma was treated as follows.

Presentation Right supra-clavicular mass. Originally had nodular melanoma excised from right elbow, and had high-dose interferon post-operatively. Required axillary clearance for a mass in right axilla eight months later.

Further staging was clear at that time. Presented one year later with a fixed inoperable mass in right supra-clavicular area.
Treatment IL-2 and Taurolidine
Regimen Interleukin-2
  Day 1: 18 million units/m² IL-2 infusion over 6 hours
  Day 2: 18 million units/m² IL-2 infusion over 12 hours
  Day 3: 18 million units/m² IL-2 infusion over 24 hours
  Days 4-7: 18 million units/m² IL-2 infusion over 78 hours
  Taurolidine
  Taurolidine 2% 250 ml infusion over twelve hours, daily during IL-2 administration
  Completed five courses of the above
After one year, the patient is alive and well, with no evidence of disease on imaging.

EXAMPLE 2

A 50 year old patient diagnosed with metastatic renal cell carcinoma was treated as follows.
  Presentation Haemoptysis—2° to pulmonary metastases. Noted to have hepatic metastases, in addition to a large mass in the left kidney.
  Treatment IL-2 and Taurolidine
  Regimen Interleukin-2
    Day 1: 18 million units/m² IL-2 infusion over 6 hours
    Day 2: 18 million units/m² IL-2 infusion over 12 hours
    Day 3: 18 million units/m² IL-2 infusion over 24 hours
    Days 4-7: 18 million units/m² IL-2 infusion over 78 hours
    Taurolidine
    Taurolidine 2% 250 ml infusion over two hours, twice daily during IL-2 administration
    Completed five courses of the above
Further treatment Left radical nephrectomy
After five years, the patient is alive and well, with no evidence of disease on imaging.

EXAMPLE 3

A male patient who had recurrent nodular melanoma after interferon treatment was subsequently treated with Interleukin-2 and Taurolidine as follows:
  Presentation Recurrence of nodular melanoma lesion in right shoulder.
  Treatment IL-2 and Taurolidine
  Regimen Interleukin-2
    Day 1: 36 million units/m2 IL-2 infusion over 6 hours
    Day 2: 36 million units/m2 IL-2 infusion over 12 hours
    Day 3: 36 million units/m2 IL-2 infusion over 24 hours
    Days 4-7: 36 million units/m2 IL-2 infusion over 78 hours
    Taurolidine
    Taurolidine 2% 250 ml infusion over twelve hours, sequentially with IL-2 administration, during days 1-6
    Undertook five courses—during second course, treatment was interrupted and stopped at 78 hours, and during the fifth course, treatment was interrupted during day 4.
Follow-up CT scans indicated a reduction in the size of the lesion, and subsequently indicated no evidence of disease.

The invention claimed is:

1. A method of reducing toxicity of IL-2 and reducing side effects of IL-2 in a cancer patient in need of IL-2 administration, comprising administering a tumor-inhibiting amount of IL-2 to said cancer patient during a treatment period, wherein said IL-2 administration is capable of causing said toxicity and said side effects in said cancer patient, and further comprising administering to said patient an IL-2 toxicity-reducing and side effects-reducing amount of taurolidine, taurultam, or a combination thereof, during said treatment period, wherein said toxicity and said side effects of said IL-2 in said cancer patient are reduced, wherein said IL-2 is administered to said patient in an amount of about 18 million U/m² body surface area of said patient per day, and said taurolidine is administered to said patient in an amount of about 250 ml 2% by weight taurolidine solution twice daily.

2. The method of claim 1 wherein said patient has a cancer which is a glioma, neuroblastoma, astrocytoma, carcinomatous meningitis, breast cancer, ovarian cancer, colon cancer, prostate cancer, pancreatic cancer, central nervous system (CNS) cancer, liver cancer, lung cancer, gastric cancer, esophageal cancer, urinary bladder cancer, leukemia, lymphoma, melanoma, renal cell cancer or metastases thereof.

3. The method of claim 2 wherein said cancer is a melanoma.

4. The method of claim 2 wherein said cancer is metastatic malignant melanoma.

5. The method of claim 2 wherein said cancer is metastatic renal cell carcinoma.

6. The method of claim 1, wherein said IL-2 and said taurolidine, taurultam or combination thereof are administered simultaneously.

7. A method of reducing toxicity of IL-2 and reducing side effects of IL-2 in a cancer patient in need of IL-2 administration, comprising administering a tumor-inhibiting amount of IL-2 to said cancer patient during a treatment period, wherein said IL-2 administration is capable of causing said toxicity and said side effects in said cancer patient, and further comprising administering to said patient an IL-2 toxicity-reducing and side effects-reducing amount of taurolidine, taurultam, or a combination thereof, during said treatment period, wherein said toxicity and said side effects of said IL-2 in said cancer patient are reduced, wherein said IL-2 is administered to said patient in an amount of about 36 million U/m² body surface area of said patient per day.

8. The method of claim 7 wherein said patient has a cancer which is a glioma, neuroblastoma, astrocytoma, carcinomatous meningitis, breast cancer, ovarian cancer, colon cancer, prostate cancer, pancreatic cancer, central nervous system (CNS) cancer, liver cancer, lung cancer, gastric cancer, esophageal cancer, urinary bladder cancer, leukemia, lymphoma, melanoma, renal cell cancer or metastases thereof.

9. The method of claim 8 wherein said cancer is a melanoma.

10. The method of claim 8 wherein said cancer is metastatic malignant melanoma.

11. The method of claim 8 wherein said cancer is metastatic renal cell carcinoma.

12. The method of claim 7, wherein said IL-2 and said taurolidine, taurultam or combination thereof are administered simultaneously.

13. A method of reducing toxicity of IL-2 and reducing side effects of IL-2 in a cancer patient in need of IL-2 administration, comprising administering a tumor-inhibiting amount of IL-2 to said cancer patient during a treatment period, wherein said IL-2 administration is capable of causing said toxicity and said side effects in said cancer patient, and further comprising administering to said patient an IL-2 toxicity-reducing and side effects-reducing amount of taurolidine, taurultam, or a combination thereof, during said treatment period, wherein said toxicity and said side effects of said IL-2 in said cancer patient are reduced, wherein said IL-2 is administered to said patient in an amount of about 18 million U/m² body surface area of said patient per day, and said taurolidine is administered to said patient in an amount of about 250 ml 2% by weight taurolidine solution 1-6 times per day.

14. A method of reducing toxicity of IL-2 and reducing side effects of IL-2 in a cancer patient in need of IL-2 administration, comprising administering a tumor-inhibiting amount of IL-2 to said cancer patient during a treatment period, wherein said IL-2 administration is capable of causing said toxicity and said side effects in said cancer patient, and further comprising administering to said patient an IL-2 toxicity-reducing and side effects-reducing amount of taurolidine, taurultam, or a combination thereof, during said treatment period, wherein said toxicity and said side effects of said IL-2 in said cancer patient are reduced, wherein said IL-2 is administered to said patient in an amount of about 18 million U/m² body surface area of said patient per day, and said taurolidine is administered to said patient in an amount of about 250 ml 2% by weight taurolidine solution twice daily.

15. A method of reducing toxicity of IL-2 and reducing side effects of IL-2 in a cancer patient in need of IL-2 administration, comprising administering a tumor-inhibiting amount of IL-2 to said cancer patient during a treatment period, wherein said IL-2 administration is capable of causing said toxicity and said side effects in said cancer patient, and further comprising administering to said patient an IL-2 toxicity-reducing and side effects-reducing amount of taurolidine, taurultam, or a combination thereof, during said treatment period, wherein said toxicity and said side effects of said IL-2 in said cancer patient are reduced, wherein said IL-2 is administered to said patient in an amount of about 36 million U/m² body surface area of said patient per day, and said taurolidine is administered to said patient in an amount of about 250 ml 2% by weight taurolidine solution 1-6 times per day.

16. A method of reducing toxicity of IL-2 and reducing side effects of IL-2 in a cancer patient in need of IL-2 administration, comprising administering a tumor-inhibiting amount of IL-2 to said cancer patient during a treatment period, wherein said IL-2 administration is capable of causing said toxicity and said side effects in said cancer patient, and further comprising administering to said patient an IL-2 toxicity-reducing and side effects-reducing amount of taurolidine, taurultam, or a combination thereof, during said treatment period, wherein said toxicity and said side effects of said IL-2 in said cancer patient are reduced, wherein said taurolidine, taurultam or combination thereof is administered as a 2% solution, intravenously or orally.

* * * * *